United States Patent [19]

Strumpf et al.

[11] Patent Number: 5,182,277
[45] Date of Patent: Jan. 26, 1993

[54] FUNGICIDES AND PLANT-GROWTH CONTROLLING AGENTS

[75] Inventors: Thomas Strumpf, Potsdam; Horst Lyr, Eberswalde; Dieter Zanke, Potsdam-Babelsberg; Gerlinde Zollfrank, Potsdam, all of Fed. Rep. of Germany; Gyula Oros; Ferenc Viranyi, both of Budapest, Hungary; Tibor Ersek, Columbia, Mo.

[73] Assignee: Chinoin Gyogyszer es Vegyeszeti Termekek Gyara R.T., Budapest, Hungary

[21] Appl. No.: 492,066

[22] Filed: Mar. 9, 1990

Related U.S. Application Data

[63] Continuation-in-part of Ser. No. 835,608, Mar. 3, 1986, Pat. No. 4,983,207, which is a continuation-in-part of Ser. No. 344,009, Apr. 26, 1989, Pat. No. 4,954,495.

[51] Int. Cl.$^5$ ............................................. A61K 31/535
[52] U.S. Cl. .................................. 514/231.2; 514/472
[58] Field of Search ...................... 514/184, 231.2, 534, 514/539, 472

[56] References Cited

U.S. PATENT DOCUMENTS 4,496,388  1/1985  Clough .................... 71/76

FOREIGN PATENT DOCUMENTS

| A-86640/82 | 7/1982 | Australia. |
| 1022068 | 6/1977 | Canada. |
| 1107639 | 8/1981 | Canada. |
| 3021068A1 | 12/1981 | Fed. Rep. of Germany. |
| 3602317A1 | 7/1987 | Fed. Rep. of Germany. |

OTHER PUBLICATIONS

Eckert et al., Investigations On New Postharvest Fungicides for Citrus Fruits in California, Proc. Int. Soc. Citriculture, pp. 804–810 (1981).
Pestic. Sci., 1982, 13, 330–339 Fisher et al. (underlying reference in Chem. Abstracts 97:140127z cited by the Examiner as Chem. Abstracts R).
The Pesticide Manual, a World Compendium, Eighth Edition, p. 344, Charles R. Worthing.
Pertanika, 6(1), 34 to 39 (1983)–Lim Tong-Kwee et al.
Acta Phytopathologica et Entomologica Hungarica, 21 (1–2), pp. 157–164 (1986) G. Oros et al.
Ann Appl. Biol. (1987), 110, 53–63 G. Oros et al.
Albert et al. CA107:193014s 1986.
BASF A.-G CA96:81338y 1982.
Eckert et al., CA100:119576r 1984.
Fischer et al., CA, 97:140127z 1982.

*Primary Examiner*—Frederick E. Waddell
*Assistant Examiner*—Russell Travers
*Attorney, Agent, or Firm*—Herbert Dubno; Jonathan Myers

[57] ABSTRACT

A synergistic plant fungicide is disclosed which comprises:
(A) a morpholine compound selected from the group consisting of:
 (a) N-tridecyl-2,6-dimethylmorpholine;
 (b) N-cyclododecyl-2,6-dimethylmorpholine;
 (c) N-alkyl($C_{12}$)-2,6-dimethylmorpholine; and
 (d) 4-(3-p-tert.-butylphenyl)-2-methylpropyl-6-cis-dimethylmorpholine; or an agriculturally acceptable salt thereof; in combination with
(B) a second compound selected from the group consisting of:
 (e) 2-chloro-N-(2,6-dimethylphenyl)-N-(tetrahydro-2--oxo-3-furanyl)-acetamide;
 (f) 2-methoxy-N-(2-oxo-1,3-oxazolidin-3-yl)-N-(2,6-dimethylphenyl)-acetamide; wherein the weight ratio of Compound (A) to Compound (B) is 20:1 to 1:2.

6 Claims, No Drawings

FUNGICIDES AND PLANT-GROWTH CONTROLLING AGENTS

CROSS REFERENCE TO RELATED APPLICATIONS

This is a continuation-in-part of copending application Ser. No. 06/835,608 filed on Mar. 3, 1986, now U.S. Pat. No. 4,983,207, which is a C-I-P of Ser. No. 07/344,009 filed Apr. 26, 1989, now U.S. Pat. No. 4,954,495.

FIELD OF THE INVENTION

The invention relates to antifungal and plant-growth controlling compositions and to their application in plant-protection.

BACKGROUND OF THE INVENTION

Alkylmorpholines are put into action to fight the true powdery mildew fungi (DE 11 64 152, DE 11 98 125, DD 140 412, DE 26 56 747). Acylanilines have found entrance as Oomycete-active fungicides into the practical plant-protection (see R. Wegler, Chemie der Pflanzenschutz and Scadlingsbekampfungsmittel, Vol. 6).

Based on the relatively narrow activity-spectrum of all these compounds different advantageous mixtures for morpholine fungicides (DD 134 040, DD 104, 416, DD 111 014, DD 116 384, DD 121 013, DE 26 33 874, DE 27 07 709, DE 27 18 721, DE 28 35 253, DD 155 481, DD 157 592) and acylanilines as well (EP 26 873, DE 30 21 068, GB 2 107 496, JP 82 128 609, EP 30 570, DE 33 01 281) have been formulated.

Nevertheless for some applications the activity, intensity and the fungicide spectrum could be improved.

OBJECT OF THE INVENTION

The object of the present invention is to find suitable combination-partners for morpholine-fungicides which lead to an increase of the fungicide activity, and inhibit the development of resistance and simultaneously control the fungal growth through intervention in the fungal metabolism.

SUMMARY OF THE INVENTION

It was found, that a mixture consisting of a fungicide from the group of morpholines (A) N-tridecyl-2,6-dimethylmorpholine (Tridemorph) (1); N-cyclododecyl-2,6-dimethylmorpholine (Dodemorph) (2); N-alkyl($C_{12}$)-2,6-dimethylmorpholine (Aldimorph) (3); 4-(3-p-tert.-butylphenyl)-2-methylpropyl-2,6-cis-dimethylmorpholine (Fenpropemorph) (4) as well as their plant physiologically acceptable salts, molecular-and addition compounds and one of the following fungicides (B) N-(2,6-dimethylphenyl)-N-furoyl-(2)-alaninemethylester (Furalaxyl) (5); N-(2,6-dimethylphenyl)-N-chloroacetyl-alaninemethylester (CGA 29 212) (6); N-(2,6-dimethylphenyl)-N-phenylacetyl-alaninemethylester (Benalaxyl) (7); 2-chloro-N-(2,6-dimethylphenyl)-N-(tetrahydro-2-oxo-3-furanyl)-acetamide (Ofurace) (8); 3-chloro-N-(tetrahydro-2-oxo-3-furanyl)-cyclopropane-carboxanilide (Cyprofuram) (9); 2-methoxy-N-(2-oxo-1,3-oxazolidin-3-yl)-N-(2,6-dimethylphenyl)-acetamide (Oxadixyl) (10); N-isoxazol-5-yl-N-(2,6-xylyl)-alaninemethylester (LAB 149 202 F) (11); N-(2,6-dimethylphenyl)-2-methoxy-N-(tetrahydro-2-oxo-3-furanyl)-)-acetamide (RE 26 745) (12); N-(2,6-dimethylphenyl)-2-methoxy-N-(tetrahydro-2-oxothien-3-yl)-acetamide (RE 26 940) (13), as active ingredients, possesses an improved fungicide activity especially against Oomycetes and is suitable for the control of plant-growth. The effects induced by the combination of the active agents are based on synergistic influences. The increased practical breadth of application of the new combinations is advantageous, which makes it possible to control the downy and powdery mildews. Moreover the probability of the appearance of resistant strains, because of the different mode of action of the two components and the differences in sensitivity of the stages of fungal life cycle, markedly decreased. The mixtures according to the invention this way represent an improvement over the prior art.

With the new combination the damaging fungi appearing on plants or on the parts of plants can be decreased. Based on the systemic properties of both components even new growing parts of plants will be protected against fungal attacks. The mixtures are efficacious against phytophathogenic fungi of the following groups: Ascomycetes (e.g. Erysiphe- and Sclerotinia-species), Oomycetes (firstly Phytophthora-, Peronospora- and Plasmopara-species) and Basidiomycetes (e.g. Rhizoetonia-species).

The combinations are employed advantageously for the control of plant-growth of cereals, vegetables and vegetable cultures as e.g. cucumbers, tomato, sun flowers, among others of cultivated plants as well as of some ornamental plants. At the employed concentrations no phytotoxic damage was observed. The seed corn's quality will not be affected disadvantageously. Further, the fungicidal effect of the components of the combinations is of importance for the safeguarding of the yield.

The mass ratio of the morpholine-fungicides and fungicides of the second group in the mixtures can be varied, between 20:1 to 1:2, especially from 20:1 to 1:1, advantageously from 10:1 to 2:1, preferred from 5:1 to 3:1.

The preparation of the enumerated morpholines (A) inclusive of its salts, molecular and addition compounds (DE 11 64 152, DE 11 73 722, DE 24 61 513, DE 11 98 125, DD 140 041, DE 26 56 747), as well as of the other known fungicides (B) (DE 25 13 788, DE 23 50 944, DD 142 042, U.S. Pat. No. 3 933 860, DE 27 24 786, FR 2 463 132, EP 26 873, DE 28 41 824, BE 871 668) is well known.

The combinations of the active ingredients according to the invention can be transferred into usual formulations as solutions, emulsion concentrates, suspensions, powders, spray powders, strewing powders, pastes, granulates, aerosols, seed corn powder etc. The formulations will include the active ingredients and can include surface active agents, solid or liquid diluents or solvents, liquefied gases under pressure and other materials as required to produce the desired formulation. The formulations are prepared by methods known per se.

Liquid solvents can be e.g.: fractions of mineral oils with a moderate to high boiling point, e.g. kerosine or Diesel-oil, oils of plant or animal origin, aliphatic, cyclic and aromatic hydrocarbons, e.g. toluene, xylene, alkylated naphthalenes, cyclohexanes, paraffin, alcohols, glycols, esters, ketones and halogenated hydrocarbons, e.g. butanol, ethyleneglycol, methylethylketone, cyclohexanone, chloroform, chlorobenzene or polar solvents, e.g. dimethyl-formamide, dimethylsulfoxide or N-methylpyrrolidone.

As liquefied gases under pressure aerosol gases are means e.g. halogenated hydrocarbons, propane, butane and carbon dioxide. As solid carriers natural rock flours, e.g. kaoline, talc, silica, montmorillonite and diatomaceous earth and synthetic rock flours, e.g. highly dispersed silicid acid aluminum-oxide and silicates can be applied. For granulates the following materials are suitable as carriers: broken natural stones, e.g. calcite, marble, pumice-stone, dolomite, synthetic granulates from inorganic and organic flours as well as granulates from organic material, e.g. sawdusts, shells of coconut, corn-cobs and tobacco stems.

The surface-active agents act as wetting emulsifying and/or dispersing agents. Here the following compounds can be taken into consideration: alkali-, earth alkali- and ammonium salts of ligninsulphonic acid, naphthalene-sulphonic acid, phenolsulphonic acid, alkylarylsulphonates, alkylsulphates, alkylsulphonates, alkali- and earth alkali salts of dibutylnaphthalene-sulphonic-acid, laurylethersulphate, fatty alcohol sulphates, alkali- and earth alkali salts of fatty acids, salts of sulphated hexadecanols, heptadecanols, octadeconols, salts of sulphated fatty alcohol glycolethers, condensation products of sulphonated naphthalenes and naphthalene derivatives with formaldehyde, condensation products of naphthalenes of naphthalenesulphonic acids respectively with phenol and formaldehyde, polyoxyethylene-octyl-phenolether, ethoxylated isooctylphenol, octylphenol, nonylphenol, alkylphenolpolyglycolether, tributylphenylpolyglycolether, alkylaryl-polyether alcohols, isotridecyl alcohol, fatty alcohol ethyleneoxide-condensates, ethoxylated Rizinus-oil, polyoxyethylenealkylether, ethoxylated polyoxypropylene, lauryl-alcoholpolyglycolether-acetil sorbitester, lignin, sulphite waste alkalis and methyl cellulose.

The formulations may further contain adhesion agents as carboxy methylcellulose, natural or polymers as gum arabic, polyvinylalcohol or polyvinylacetate and the like.

The formulations contain generally 1 to 95% by weight of the active ingredients (A)+(B).

Aqueous forms of application can be prepared from emulsion concentrates, suspensions, spray powders (strewing powders) etc. by addition of water. The preparation of emulsions or oil dispersions is carried out by dissolving the active ingredients and other additives in oil or a solvent or homogenization in water by means of wetting, dispersing- or emulsifying agents.

The application takes place in the usual manner, e.g. by immersion, pouring, spraying, strewing or dusting. The applied quantities depend on the specific goal of application and generally lie between 0.5 and 5.0 kg/ha respectively 10-200 g active ingredient per 100 kg seed corn. The active agent combinations according to the invention can be mixed for the enlargement of the application breadth and plant protection with other known fungicides, herbicides, insecticides, desiccants, defoliants, growth controlling agents or fertilizers.

EXAMPLE 1

Composition of a sprinkling powder
18 weight % of Tridemorph
7 weight % of LAB 149 202 F
5 weight % of calciumligninsulphonate
5 weight % of alkylphenol-ethyleneoxide addition agent
20 weight % of silicic acid
45 weight % of kaolin

EXAMPLE 2

Composition of an emulsion-concentrate
35 weight % of Aldimorph
15 weight % Ofurace
18.5 weight % toluene
18.5 weight % cyclohexanone
10 weight % of ter. butanol
2 weight % epoxydated octylphenolether
1 weight % Tween 20 ... 80

EXAMPLE 3

Synergistic effect of mixtures from morpholine-fungicides (A) and fungicides (B) on Phytophthora cinnamomi in vitro Phytphthora cinnamomi was grown in Petri dishes on green pea agar media containing the mentioned active agents, combinations respectively in the given concentrations. The inoculation as carried out with mycelial discs. After 5 days of cultivation at 21°· C. the colony diameter was measured and the inhibition of the radial growth related to the untreated control was calculated. The synergistic effect was calculated according to COLBY.

| Cont. of Example 3 | | | |
|---|---|---|---|
| Active Agent, combination resp. | Concentration (mg/l) | Growth-inhibition (%) | Effect according to COLBY (%) |
| Tridemorph (1) | 4 | 51 | — |
| | 0.4 | 6 | — |
| | 0.04 | 1 | — |
| Dodemorph (2) | 40 | 52 | — |
| | 4 | 12 | — |
| | 0.4 | 2 | — |
| Aldimorph (3) | 40 | 64 | — |
| | 4 | 1 | — |
| | 0.4 | 1 | — |
| Aldimorph HCl (3a) | 40 | 81 | — |
| | 4 | 24 | — |
| | 0.4 | 3 | — |
| Fenpropemorph HCl (4a) | 4 | 1 | — |
| | 0.4 | 1 | — |
| Fenpropemorph-methosulphate (4b) | 0.4 | 3 | — |
| | 0.04 | 2 | — |
| Furalaxyl (5) | 1 | 69 | — |
| | 0.1 | 19 | — |
| | 0.01 | 2 | — |
| Benalaxyl (7) | 10 | 40 | — |
| | 1 | 19 | — |
| | 0.1 | 6 | — |
| Ofurace (8) | 10 | 56 | — |
| | 1 | 20 | — |
| | 0.1 | 5 | — |
| Cyprofuram (9) | 10 | 68 | — |
| | 1 | 14 | — |
| | 0.1 | 1 | — |
| LAB 149 202 F (11) | 10 | 84 | — |
| | 1 | 25 | — |
| | 0.1 | 2 | — |
| RE 26 745 (12) | 1 | 77 | — |
| | 0.1 | 12 | — |
| | 0.01 | 2 | — |
| 1 + 5 | 4 + 1 | 88 | +3 |
| | 0.4 + 0.1 | 49 | +25 |
| | 0.04 + 0.01 | 12 | +9 |
| 1 + 11 | 4 + 1 | 77 | +14 |
| | 0.4 + 0.1 | 17 | +9 |
| 2 + 7 | 40 + 10 | 97 | +26 |
| 2 + 8 | 4 + 1 | 45 | +15 |
| | 0.4 + 0.1 | 28 | +21 |
| 2 + 9 | 40 + 10 | 100 | +15 |
| 2 + 12 | 0.4 + 0.1 | 32 | +17 |
| 3 + 5 | 4 + 1 | 78 | +9 |

-continued

Cont. of Example 3

| Active Agent, combination resp. | Concentration (mg/l) | Growth-inhibition (%) | Effect according to COLBY (%) |
| --- | --- | --- | --- |
| 3 + 8 | 4 + 1 | 34 | +14 |
| 3 + 11 | 4 + 1 | 53 | +27 |
| 3a + 7 | 4 + 1 | 76 | +38 |
|  | 0.4 + 0.1 | 17 | +8 |
| 3a + 12 | 0.4 + 0.1 | 21 | +7 |
| 4a + 5 | 4 + 1 | 73 | +4 |
|  | 0.4 + 0.1 | 22 | +2 |
| 4b + 5 | 0.4 + 0.1 | 38 | +16 |
|  | 0.04 + 0.01 | 15 | +11 |

EXAMPLE 4a

The effect of LAB 149202F, tridemorph and their combination on the infection by Plasmopara halstedii in sunflower.

Sunflower seedlings were inoculated with zoospore suspension ($2.5 \times 10^5$ spores/ml) of the downy mildew fungus (Plasmopara halstedii (Farl.) Berlese et de Toni). Twenty four hours after inoculation the seedlings were immersed into the aqueous solutions of LAB 149202F, tridemorph and their combination, respectively for 18 hours. The seedlings were then planted into sterile soil and grown in greenhouse until the stage of fully developed cotyledons. The effect of fungicides on the rate of systemic infection was determined and the $ED_{50}$ level was calculated. The significance for a synergistic action was expressed as Comparative Toxicity Index (Co.T.I.) that is calculated according to the equation below:

$$CoTI = \frac{1/ED_{50}^{mixt}}{\frac{a}{ED_{50}^{A}} + \frac{b}{ED_{50}^{B}}}$$

In this equation a and b indicate the current mass parts of the active agents A and B in the combination.

A CoTI value > 1.25 means, that the synergism is significant.

The CoTI suggested by SUN, YUN-PEI:Toxicity Index - an improved method of comparing the relative toxicity of insecticides, J. Econ. Entom. 1:45-53 (1950) was applied according to the interpretation of BANKI,L.: Bioassay of pesticides in the laboratory. Research and quality control. Akadémia Kiadó, Budapest 1978. Two other models for calculation the synergistic interaction were applied, too. One of them was the widely used Colby's formula:

$$FTE_{exp} = FTE_A + FTE_B - \frac{FTE_A \times FTE_B}{100}$$

where the Toxic Effects (FTE) of the active ingredients A and B are given at %-s of the inhibition rates estimated at the same concentration level, respectively according to COLBY, S.R.: Calculating synergistic and antagonistic responses of herbicide combinations. Weeds 15:20-22 (1967). the increase in effectivity was also determined at a rate equal to the total amount of chemicals combined (i.e. corresponding to the concentration level when the compound is used separately (alone) for the determination of maximum response value of the fungi to the chemicals, according to the HORSFALL's model of the demonstration of synergistic interaction).

Results are shown in the Tables

TABLE

Demonstration of synergistic interaction on the comparative concentration level*

| Active Ingredient, combination, resp. | Conc. mg/L | Inhibition % | Synergistic effect** % A | B |
| --- | --- | --- | --- | --- |
| 1. Tridemorph | 2.5 | 0 | — | — |
| 2. LAB 149202F | 0.1 | 0 | — | — |
| 3. " | 0.25 | 4 | — | — |
| 4. " | 0.5 | 20 | — | — |
| 5. " | 1.0 | 60 | — | — |
| 6. Tridemorph + LAB 149202F | 0.08 0.02 | 25 | +25 | +25 |
| 7. Tridemorph + LAB 149202F | 0.20 0.05 | 48 | +48 | +44 |
| 8. Tridemorph + LAB 149202F | 0.40 0.10 | 61 | +60 | +41 |
| 9. Tridemorph + LAB 149202F | 0.80 0.20 | 82 | +78 | +22 |

*Colby's model
**in the case A the synergistic effect was calculated by means of Colby's formula, in the case B the increase in effectivity was determined at a rate equal to the total amount of chemicals combined.

Synergistic experiment on greenhouse level in the system sunflower -Plasmopara halstedii

| Active ingredient, combination, resp. | $ED_{50}$ (Mg/l) | CoTI |
| --- | --- | --- |
| 1. Tridemorph | 1000+ | — |
| 2. LAB 149202F | 0.85 | — |
| 3. 1 + 2 (4:1, w/w) | 0.26 | 3.25 |

+The phytotoxic effect inerferes with the exact determination of $ED_{50}$ value.

EXAMPLE 4b

Synergistic effect of mixtures from morpholine (fenpropimorph and its derivates) and phenylamide (furalaxyl) fungicides on the vegetative growth of Phytophthora species in vitro.

The isolates were grown in 9 cm Petri dishes on green pea agar medium at a standard incubation temperature of 18°-20° C. in the darkness. Cultural techniques and assessments were made according to ROOKE, D.M. and SHATTOCK, R.C. (1983): Effect of chloramphenicol and streptomycin on developmental stages of Phytophthora infestans. J. Gen Microbiol. 129, 3401-3410. The inhibition of radial growth was calculated in % as compared to the untreated control, and the efficacy of fungicides and their mixtures was characterized by an $ED_{50}$ value (in mg/L), calculated from basic data, using a curve-fitting method based on log/logistic function.

The degree of synergistic interaction was characterized with a comparative toxicity index (CoTI), suggested by SUN, YUN-PEI: Toxicity Index - an improved method of comparing the relative toxicity of insecticides. J. Econ. Entomol. 1:45-53 (1950), and applied according to the interpretation of BANKI, L.: Bioassay of pesticides in the laboratory. Research and quality control. Akademia Kiado, Budapest 19789. An another model for the calculation of the synergistic interaction, the widely used Colby formula was applied. The increase in effectivity was also determined at a rate equal to the total amount of chemicals combined (i.e. corresponding to the concentration level when the compound is used separately (alone) for the determination of maximum response value of the fungi to the chemicals, according to the Horsfall's model of the demonstration of synergistic interaction.

Results are shown in the Table.

TABLE

Synergistic effect of mixtures from furalaxyl and various morpholine fungicides on the vegetative growth of Phytophthora species in vitro.

| Active agent, combination, respectively (ratio) | Sensitivity of Phytophthora species $ED_{50}$ mg/L (CoTI) | | |
|---|---|---|---|
| | cactorum | cinnamomi | magasperma |
| 1. Furalaxil | 0.17 | 0.44 | 0.15 |
| 2. Fenpropimorph | 174.95 | 29.86 | 23.74 |
| 3. Fenpropimorph.HCl | 98.63 | 85.59 | 111.36 |
| 4. Fenpropimorph-methosulphate | 35.62 | 295.29 | 79.42 |
| 5. 1 + 2 (1:4) | 0.11 (1.49) | — | — |
| 6. 1 + 3 (1:4) | 0.09 (1.92) | 0.25 (1.73) | 0.06 (2.50) |
| 7. 1 + 4 (1:4) | 0.08 (2.09) | 0.09 (4.56) | 0.05 (3.26) |

| Active agent, combination, respectively | Concentr. mg/L | Inhibition of radial growth+ % | Synergistic effect++ % | |
|---|---|---|---|---|
| | | | A | B |
| 1. Furalaxyl | 0.1 | 19 | — | — |
| 2. " | 0.5 | 53 | — | — |
| 3. Fenpropimorph+++ | 0.5 | 0 | — | — |
| 4. Fenpropimorph+++ Furalaxyl | 0.4 0.1 | 80 | +61 | +27 |

+The indicator organism was Phytophthora cinnamomi
++in the case A the synergistic effect was calculated by means of Colby's formula, in the case B the increase in effectivity was determined at a rate equal to the total amount of chemicals combined.
+++Fenpropimorph methosulphate was applied.

EXAMPLE 4c

Synergistic curative effect of mixtures from morpholine (A) and acylalanine (B) fungicides on *Plasmopara halstedii* downy mildew of sunflower.

Sunflower seeds (Helianthus annus cv. GK-70) were infected with a suspension of zoospores of *Plasmopara halstedii* ($2.5 \times 10^5$ cell/ml). After 24 hours the seedlings were immersed into the aqueous solutions (emulsions) of various concentrations of the mentioned substances (from 50 EC) for 18 hours.

| Active agent resp. combination | $ED_{50}$ (mg/l) | Co. T.I. |
|---|---|---|
| Aldimorph (3) | | 1040.0$^{x/}$ |
| Aldimorph HCl (3a) | 771.0$^{x/}$ | — |
| RE 26745 (12) | | 33.0 |
| 3 + 12 (3 + 1) | 5.4 | 5.57 |
| 3a + 12 (3 + 1) | 16.1 | 1.82 |

$^{x/}$phytotoxic

EXAMPLE 5

Synergistic effect of mixtures from morpholine (A) and acylalanine (B) fungicides on the vegetative growth of some Phytophthora species in vitro.

The fungi were—as described in Example 3—grown on green-pea agar plates containing the active ingredients. The $ED_{50}$ values were calculated based on the inhibition of the radial growth compared to the untreated control. The mixing ratio in all of the cases was 4:1 weight parts. The synergistic effect was expressed as CoTI according to Example 4a, where values from $1.0\pm0.25$ mean an additive effect, and those from $>1.25$ a significant synergistic effect.

| Combination | P. catorum $ED_{50}$ (Co. T.I.) (mg/l) | P. cambivora $ED_{50}$ (Co T.I.) (mg/l) |
|---|---|---|
| Tridemorph (1) | 24.2 | 12.4 |
| Dodemorph (2) | 47.3 | 258.0 |
| Aldimorph (3) | 32.7 | 36.2 |
| Aldimorph HCl (3a) | 34.6 | 23.6 |
| Fenpropemorph (4) | 175.0 | 6.41 |
| Furalaxyl (5) | 0.17 | 0.05 |
| Benalaxyl (7) | 1.8 | 0.25 |
| Ofurace (8) | 0.79 | 1.12 |
| Cyprofuram (9) | 5.0 | 2.8 |
| Oxadixyl (10) | 0.12 | 0.45 |
| LAB 149 202 F (11) | 0.15 | 0.08 |
| RE 26 940 (13) | 0.22 | 0.31 |
| 1 + 10 | 0.19 (0.62) | 0.10 (3.93) |
| 1 + 11 | 0.09 (1.63) | 0.73 (0.11) |
| 2 + 10 | 0.02 (5.94) | 0.09 (4.97) |
| 3 + 5 | 0.11 (1.51) | 0.07 (0.71) |
| 3 + 7 | 1.22 (1.21) | — — |
| 3 + 8 | 1.37 (0.53) | 0.75 (1.33) |
| 3 + 9 | 2.3 (1.35) | 2.4 (0.89) |
| 3a + 9 | 1.4 (2.26) | 0.91 (2.09) |
| 3a + 13 | 0.27 (0.80) | — — |
| 4 + 10 | 0.02 (5.98) | 0.22 (1.60) |

| Active agent, combination resp. | P. citricola | P. parasitica var. nicotainae |
|---|---|---|
| Tridemorph (1) | 3.9 | 56.7 |
| Dodemorph (2) | 36.9 | 124.3 |
| Aldimoroph (3) | 32.5 | 517.6 |
| Aldimorph HCl (3a) | 11.0 | 162.9 |
| Fenpropemorph (4) | 29.9 | 142.7 |
| Furalaxyl (5) | 0.21 | 0.21 |
| Benalaxyl (7) | 6.1 | 5.5 |
| Ofurace (8) | 6.84 | 14.26 |
| Cyprofuram (9) | 32.0 | 9.9 |
| Oxadixyl (10) | 0.49 | 0.13 |
| LAB 149 202 F (11) | 0.34 | 0.16 |
| RE 26 940 (13) | 1.67 | — |
| 1 + 10 | 0.32 (0.93) | 0.24 (0.54) |
| 1 + 11 | — — | — — |
| 2 + 10 | 0.15 (3.10) | 0.09 (1.44) |
| 3 + 5 | 3.11 (0.07) | 1.23 (0.17) |
| 3 + 7 | 1.58 (2.21) | 1.36 (3.88) |
| 3 + 8 | 0.85 (4.37) | 5.15 (2.49) |
| 3 + 9 | 7.4 (0.88) | 9.6 (0.96) |
| 3a + 9 | 1.69 (1.50) | 3.2 (2.69) |
| 3a + 13 | 0.78 (1.33) | — — |
| 4 + 10 | 2.62 (0.18) | 0.19 (0.68) |

EXAMPLE 6

Inhibition of the epicotyl longation of soy-bean *Glycine max* by mixtures from morpholine (A) and acylalanine (B) fungicides (immersion of the seed).

Soy-bean seeds c.v. (Harosoy) were dressed with the agents in the given quantity of application and one week after treatment they were sown (50 seeds of each application). After three weeks the length of epicotyl was measured.

| Active agent, combination | Concentration (g/100 kg of seeds) | Length of the epicotyles (mm) | Difference comp. to the control (mm) | Effect according to COLBY |
|---|---|---|---|---|
| untreated control | — | 147 | — | — |
| Tridemorph- | 40 | 122 | −25 | — |

| Active agent, combination | Concentration (g/100 kg of seeds) | Length of the epi-cotyles (mm) | Difference comp. to the control (mm) | Effect according to COLBY |
|---|---|---|---|---|
| methosulphate (1b) Fenpropemorph methosulphate (4b) | 40 | 39 | −108 | — |
| Benalaxyl (7) | 10 | 151 | +4 | — |
| LAB 149 202 F (11) | 10 | 140 | −7 | — |
| RE 26 745 (12) | 10 | 155 | +8 | — |
| 1b + 11 | 40 + 10 | 86 | −61 | 31 |
| 1b + 12 | 40 + 10 | 111 | −36 | 21 |
| 4b + 7 | 40 + 10 | 32 | −115 | 15 |
| 4b + 12 | 40 + 10 | 18 | −129 | 38 |

EXAMPLE 7

Growth control of tomato-plants *Solanum lycopersicum* by mixtures of morpholine (A) and acylalanine (B) fungicides.

The enumerated active agents were formulated one by one and in combination as 25 WP, suspended in water and sprayed run off on tomato plants (c.v. Harzfeuer) in the four-leaf stage (20 plants in each application). After cultivation for 12 days in a green-house the dry-weight was determined and compared with that of the untreated control.

| Active agent, combination resp | conc. (mg/l) | dry-weight (g) | increase of the dry-weight (%) |
|---|---|---|---|
| Untreated control | 0 | 1.36 | 100 |
| Tridemorph (1) | 0.1 | 1.48 | 109 (−) |
| Tridemorph HCl (1a) | 0.1 | 1.56 | 115 (−) |
| Aldimorph (3) | 0.1 | 1.51 | 111 (−) |
| Aldimorph HCl (3a) | 0.1 | 1.53 | 112 (−) |
| Fenpropemorph (4) | 0.1 | 1.53 | 112 (−) |
| Fenpropemorph HCl (4a) | 0.1 | 1.50 | 110 (−) |
| Ofurace (8) | 0.05 | 1.33 | 98 (−) |
| Cyprofuram (9) | 0.05 | 1.32 | 97 (−) |
| LAB 149 202 F (11) | 0.05 | 1.39 | 102 (−) |
| RE 26 745 (12) | 0.03 | 1.44 | 106 (+) |
| 1 + 12 | 0.01 + 0.03 | 1.65 | 121 (+) |
| 1a + 12 | 0.01 + 0.03 | 1.58 | 116 (+) |
| 3 + 8 | 0.01 + 0.05 | 1.66 | 122 (+) |
| 3 + 9 | 0.01 + 0.05 | 1.64 | 121 (+) |
| 3 + 11 | 0.01 + 0.05 | 1.63 | 120 (+) |
| 3 + 12 | 0.01 + 0.03 | 1.66 | 122 (+) |
| 3a + 12 | 0.01 + 0.03 | 1.78 | 131 (+) |
| 4 + 12 | 0.01 + 0.03 | 1.66 | 122 (+) |
| 4a + 12 | 0.01 + 0.03 | 1.68 | 123 (+) |

(+) Difference to the control is significant (Pi = 5%)
(−) Difference to the control is not significant (Pi < 5%)

EXAMPLE 8

Joint action of morpholine (tridemorph) and phenylamide (benalaxyl) fungicides on the zoospore release of *Pseudoperonospora cubensis* (Berk. et Curt) Rostow.

P. cubensis (Oomycetes, Peronosporales, Peronosporaceae) is an obligate parisitic fungus, causative agent of destructive disease of cucurbitaceous plants. Like other peronosporaceous fungi (downy mildews) and Phytophthoras, this pathogen also spreads through the air by zoosporangia.

The experiments were carried out with zoosporangia of *P. cubensis* collected in a greenhouse from the infected cucumber plants. The examination was carried out according to the methods described in OROS. G. and VIRANYI, F. (1986: Acta Phytopathologica et Entomologica Hungarica, 21:157–164). The efficacy was expressed as the percent of inhibition.

| | | RESULTS | | |
|---|---|---|---|---|
| | Treatment | | | |
| No. | Substances | Concentration mg/l | Inhibition Rate (%) | −MRV |
| 1. | Tridemorph | 100 | 69 | |
| 2. | Tridemorph | 500 | 93 | |
| 3. | Benalaxyl | 100 | 61 | |
| 4. | Benalaxyl | 500 | 97 | |
| 5. | Benalaxyl + Tridemorph | 20 } 100 80 | 92 | 23 |
| 6. | Benalaxyl + Tridemorph | 100 } 500 400 | 100 | 3 |

$LSD_{5\%} = 2.5$
MRV = Maximum response value according to Horsfall's model for demonstration of synergistic interaction.

CONCLUSION

Tridemorph and benalaxyl synergistically interact in the inhibition of asexual spores of *P. cubensis*, a peronosporaceous fungus.

EXAMPLE 9

Joint action of morpholine (tridemorph) and phenylamide (benalaxyl) fungicides on the vegetative growth of Phytophthora spp. (Oomycetes, Peronosporales, Pythiaceae).

*Phytophthora parasitica* f. sp. nicotianae var. tomato and *P. citricola* both are facultatively parasitic fungi able to infect their hosts either with mycelia or with zoosporangia (soil borne and air borne infections, respectively) causing serious loss of the yield before or after the harvesting.

The inhibition of vegetative growth of both fungi was tested. The efficacy was expressed in the percent of inhibition.

| | | RESULTS | | | |
|---|---|---|---|---|---|
| | Treatment | | | | |
| | | Conc. | Inhibition of the growth of | | |
| No. | Substance | mg/L | P. citricola | −MRV | P. parasitica | −MRV |
| 1. | Tridemorph | 1 | 0 | | 3 | |

-continued

RESULTS

| Treatment | | | Inhibition of the growth of | | |
|---|---|---|---|---|---|
| No. | Substance | Conc. mg/L | P. citricola | −MRV | P. parasitica | −MRV |
| 2. | " | 5 | 14 | | 9 | |
| 3. | " | 10 | 27 | | 14 | |
| 4. | " | 50 | 75 | | 32 | |
| 5. | " | 100 | 93 | | 40 | |
| 6. | Benalaxyl | 0.5 | 13 | | 17 | |
| 7. | " | 1 | 17 | | 22 | |
| 8. | " | 5 | 44 | | 40 | |
| 9. | " | 10 | 64 | | 60 | |
| 10. | " | 50 | 92 | | 90 | |
| 11. | " | 100 | 97 | | 98 | |
| 12. | T + B (4:0) | 0.5 | 24 | +11 | 25 | +8 |
| 13. | T + B (4:0) | 1 | 35 | +18 | 37 | +15 |
| 14. | T + B (4:0) | 5 | 74 | +30 | 85 | +45 |
| 15. | T + B (4:0) | 10 | 96 | +32 | 95 | +35 |
| 16. | T + B (4:0) | 50 | 100 | +8 | 100 | +10 |

MRV = Maximum response value according to the Horsfall's model for the demonstration of synergistic interaction. The efficacy of combinations has been compared to that of the more potent partner.
T = tridemorph B = benalaxyl

CONCLUSION

Tridemorph and Benalaxyl synergistically interact in the inhibition of the vegetative growth of Phytophthoras.

EXAMPLE 10

The effect of benalaxyl, tridemorph and their combination on the vegetative growth of Phytophthora citricola (Peronosporales).

The fungus was grown in 9 cm Petri dishes on green pea agar medium at a standard incubation temperature of 18°-20° C. in the darkness. Cultural techniques and assessments were made according to ROOKE, D.M. and SHATTOCK, R.C. (1983): J. Gen. Microbiol., 129:3401-3410.

The inhibition of radial growth was calculated in % as compared to the untreated control.

| | Results: | | |
|---|---|---|---|
| Active agent, combination, resp. | Concentr. mg/l | Inhibition of radial growth % | Synergistic effect % |
| 1. Tridemorph | 5 | 14 | |
| 2. Benalaxyl | 5 | 44 | |
| 3. 1 + 2 (4:1) | 5 | 74 | +30 |

$LSD_{5\%}$ = 4.2

EXAMPLE 11

Comparative study of antifungal activity of tridemorph, benalaxyl and their mixtures against sunflower downy mildew (SDM).

The sunflower cultivar, GK-70, highly susceptible to sunflower downy mildew and a methalaxyl-sensitive isolate of Plasmopara halstedii [Farlow] Berlese et de Toni (Oomycetes, Peronosporales) originating from field collection and maintained in the glasshouse on seedlings of sunflower were used throughout this study, according to OROS & VIRANYI (1987): Ann appl. Biol., 110:53-63.

Fungicide treatments

The germlings infected as described above were maintained in the glasshouse under the same conditions for 6 days after planting, and then sprayed run off with fungicides and Assessment of fungicidal efficacy:

The seedlings 2 days after treatment were transferred overnight (approximately 14-18 h) to a humid chamber at 18°-20° C. This induced sporulation of the fungus. To determine the intensity of sporulation, a 0-4 scale was used where the proportion of cotyledon area covered by zoosporangiophores was graded as follows: 0, no sporulation; 1-4, sporulation appearing on <¼, ¼ - ½, ½ - <4/4 and 4/4 of the totally cotyledon area, respectively and SDM infection rate was calculated by using McKinney's formula. Inhibition of sporulation was calculated as a percentage of the untreated control. Methods over than detailed here are described elsewhere (OROS & VIRANYI (1987): Ann appl. Biol., 110:53-63.

The significance of differences were proved either by F- or t- distributions according to G. M. CLARKE (1980): Statistics and Experimental Design, 2nd Edition, Edward Arnold (Publishers) Ltd. London, P=5% was chosen as a limit of accepted probability. Three different models were used for evaluating the character of interaction:

A) COLBY's model compares the efficacy of a particular fungicide combination to the least effect calculated from the efficacies of each single fungicide component applied alone.

B) HORSFALL's model makes a comparison between the effect of a combination and that of the most effective single component used alone at the same mass part (dosage rate).

C) Comparison to the most potent treatment: All treatments within an experiment are compared to the most effective one and those are considered to be of equal value that show no significant difference by any accepted data analysis system at usual level of significance (P= <10% for field experiments. P= <5% for glasshouse and laboratory (in vitro) experiments.

Table of Example 11

Demonstration of joint action against sunflower downy mildew of the mixtures from benalaxyl and tridemorph.

(Comparing the experimental models for revealing synergetic action for curative treatment.)

Table of Example 11

| No. | Compounds Mixtures Respectively | Conc. mg/L | Inhibitory effect % | Models for Comparison A | B | C |
|---|---|---|---|---|---|---|
| 1. | Benalaxyl | 1.0 | 0 | — | — | −33.0 |
| 2. | Benalaxyl | 2.0 | 9.5$^a$ | — | — | −32.0 |
| 3. | Benalaxyl | 3.0 | 12.0$^{ab}$ | — | — | −22.0 |
| 4. | Benalaxyl | 5.0 | 15.0$^{bc}$ | — | — | −19.0 |
| 5. | Benalaxyl | 7.0 | 19.0 | — | — | −14.0 |
| 6. | Benalaxyl | 10.0 | 20.5 | — | = | −11.0 |
| 7. | Tridemorph | 10.0 | 0 | — | −20.5 | −34.0 |
| 8. | Benalaxyl + Tridemorph | 1.0 9.0 | 9.0$^a$ | +9.0* | −11.5 | −25.0 |
| 9. | Benalaxyl + Tridemorph | 2.0 8.0 | 20.5 | +11.0* | = | −11.0 |
| 10. | Benalaxyl + Tridemorph | 3.0 7.0 | 27.5$^a$ | +15.5* | 7.0* | −6.5 |
| 11. | Benalaxyl + Tridemorph | 4.0 6.0 | 31.5 | +18.0* | +11.0* | −2.5* |
| 12. | Benalaxyl + Tridemorph | 5.0 5.0 | 34.0 | +19.0* | +13.5* | = |
| 13. | Benalaxyl + Tridemorph | 6.0 4.0 | 28.0$^a$ | +11.0* | +7.5* | −6.0* |
| 14. | Benalaxyl + Tridemorph | 7.0 3.0 | 18.0 | −1.0 | −1.5* | −16.0 |
| 15. | Benalaxyl + Tridemorph | 9.0 1.0 | 20.0 | −0.5 | −0.5* | −14.0 |

$^+$ = The values of efficacy (% of inhibition) labeled by the same letter are not different significantly:
LSD$_{5\%}$ = 4.3 (F = 21.4 > F = P0.001 = 7.8) for benalaxyl;
LSD$_{5\%}$ = 2.3 (F = 53.9 > F = P0.001 = 17.8) for benalaxyl with tridemorph.
$^{++}$ = For comparing differences in SDM response to various treatments the COLBY's model (A), the relation to both maximum response value (B) and most potent treatment (C) were used.
The values labeled by asterisks, as a result of increased efficacy due to mixing tridemorph with benalaxyl, are not significantly different within the same column (P < 5%).

EXAMPLE 12

Comparative study of antifungal activity of tridemorph, benalaxyl and their mixtures against root rot of pea.

The pea seeds (*Pisum sativum* L. cv Rhone dwarf) were dressed with fungicides and 6 days later were sown in soil infested with Pythium spp. The efficacy of treatments was evaluated 14 days after appearance of the first seedlings. The number of healthy plant individuals was counted and the proportion (%) calculated.

The efficacy of treatments was calculated as follows:

$$\text{Efficacy (\%)} = \frac{100 \times (100 - X_{ij})}{(100 - K)}$$

where $X_{ij}$ and K are the proportion of healthy plants in the $i^{th}$ treatment with $j^{th}$ fungicide and that of the untreated control, respectively.

Results:

| No. | Treatments Compounds, combinations | Dosage mg/kg | Efficacy % | −MRV |
|---|---|---|---|---|
| 1. | Tridemorph | 1000 | 0 | — |
| 2. | Benalaxyl | 1000 | 67 | — |
|  |  | 500 | 44 | — |
|  |  | 250 | 17 | — |
|  |  | 125 | 0 | — |
| 3. | 1 + 2 (4:1) | 1000 | 100 | +33 |
|  |  | 500 | 98 | +54 |
|  |  | 250 | 44 | +27 |
| 4. | 1 + 2 (7:3) | 1000 | 100 | +33 |
|  |  | 500 | 100 | +56 |
|  |  | 250 | 56 | +39 |

MRV = Maximum Response Value

EXAMPLE 13

The efficacy of seed treatments against downy mildew of soybean (*Peronospora manshurical*)

The seeds of soybean (Glycine max L. cv Harosoy) were dressed and sowen by the usual way. The efficacy was checked at two leaf stage (for infection rate) and after harvesting (for yield). The rate of use was 350 g of active substance per 100 kg of seed in each case.

| No. | Treatments (ratio) | Results: Inhibition % | Yield t/ha | (+ %) |
|---|---|---|---|---|
| 1. | Control | — | 0.990 | — |
| 2. | Metalaxyl$^a$ | 80 | 1.142 | (15.4) |
| 3. | Tridemorph$^a$ | — | 0.975 | (−1.5) |
| 4. | Benalaxyl$^a$ | 43 | 1.005 | (1.5) |
| 5. | 3 + 4 (3:1)$^b$ | 92 | 1.195 | (20.7) |
| 6. | 3 + 4 (4:1)$^b$ | 87 | 1.138 | (14.9) |

$^a$The commercial form Apron 35 sd (metalaxyl), Calixin 75 ec (tridemorph) and Galben 25 wp (benalaxyl) were applied.
$^b$The ratio of active ingredients (w/w) is concerned.

EXAMPLE 14

Synergistic effect of tridemorph and benalaxyl against *Phytophthora infestans* (in vitro)

*Phytophthora infestans* was grown in Petri dishes on green pea agar (GPA) media and discs of 7 mm in diameter were cut out of the edge of one weak old colony. These were put onto the surface of GPA media plates containing active ingredients at appropriate concentrations and kept there 6 days. Then the inocula were transferred onto GPA media free from fungicides (one disc per plate) and the residual activity was characterized by the retardation (%) of radial growth as compared to the untreated control.

The character of interaction was evaluated according to HORSFALL's model.

The inhibition of vegetative growth of both fungi was treated as described in Example 4b. The efficacy was expressed in the percent of inhibition.

| | | | RESULTS | | | |
|---|---|---|---|---|---|---|
| | Treatment | Conc. | Inhibition of the growth of | | | |
| No | Substances | mg/L | P. citricola | −MRV | P. parasitica | −MRV |
| 1. | Tridemorph | 50 | 75 | | 32 | |
| 2. | Tridemorph | 100 | 93 | | 40 | |
| 3. | Cyprofuram | 50 | 61 | | 80 | |
| 4. | Cyprofuram | 100 | 83 | | 89 | |
| 5. | Tridemorph + Cyprofuram | 40 / 10 | 50 93 | +18 | 91 | +11 |
| 6. | Tridemorph + Cyprofuram | 80 / 20 | 100 100 | +7 | 100 | +11 |

$LSD_{5\%} = 5.4$
MRV = Maximum response value according to the Horsfall's model for demonstration synergistic interaction. The efficacy of combinations has been compared to that of the more potent partner.

| | Treatment | Results: | | |
|---|---|---|---|---|
| No. | combinations | Compounds Dose | Inhibition % | −MRV |
| 1. | Tridemorph | 50 — | 33 | — |
| 2. | Benalaxyl | 50 | 49 | — |
| 3. | Tridemorph + Benalaxyl | 40 +10 = 50 | 100 | +51% |

MRV = Maximum Response Value

EXAMPLE 15

Joint action of morpholine (aldimorph) and phenylamide (cyprofuram) fungicides on the sporulation of *Plasmopara halstedii* (Peronosporales) (leaf treatment—curative action).

Sunflower seedlings were infected and maintained as described earlier (OROS and VIRANYI (1987): Ann. appl. Biol. 110:53-63).

The treatment and other measures were made as described in Example 11.

The inhibition rate was calculated in relation to the untreated control.

| | | Results: | | |
|---|---|---|---|---|
| | Compounds, mixtures, | Concentration | Inhibition | Synergistic |
| No | resp. | mg/L | rate % | effect % |
| 1. | Aldimorph | 50 | 0 | |
| 2. | Cyprofuram | 50 | 45 | |
| 3. | 1 + 2 (7:5) | 50 | 82 | +37 |

$LSD_{5\%} = 6$

EXAMPLE 16

Joint action of morpholine (tridemorph) and phenylamide (cyprofuram) fungicides on the vegetative growth of Phytophthora species (Oomycetes, Peronosporales, Pythiaceae).

*Phytophthora parasitica* f.sp. nicotianae var. tomato and *P. citricola* both are facultatively parasitic fungi (Oomycetes, Peronosporales) able to infect their hosts either through the soil with vegetative mycelia or with zoosporangia dispersed by wind (airborn infection) causing root rot, leaf-spots and serious loss of yield in infected areas.

CONCLUSION

Tridemorph and cyprofuram synergistically interact in the inhibition of the vegetative growth of Phytophthoras.

EXAMPLE 17

Joint action of morpholine (tridemorph) and pheynlamide (cyprofuram) fungicides on the sporulation of sunflower downy mildew (leaf treatment-curative action).

Sunflower downy mildew caused by *Plasmopara halstedii* (Oomycetes, Peronosporales, Peronosporaceae) is an obligately parasitic fungus mainly introduced to new areas with infected seeds, and distributed among plant-individuals by wind, infected them through all parts. Therefore the inhibition of sporulation is an important measure of the control of this pathogen.

Sunflower seedlings were infected, and maintained as described in (Oros and Virányi (1987): Ann. appl. Biol. 110:53-63). All other measures were made as described in the Example No. 4a. The efficacy was expressed in the percent of inhibition.

| | | RESULTS | | |
|---|---|---|---|---|
| | Treatments | Concentration | Inhibition | |
| No. | Substances | mg/L | % | −MRV |
| 1. | Tridemorph | 50 | 0 | |
| 2. | Cyprofuram | 100 | 54 | |
| 3. | Cyprofuram | 30 | 14 | |
| 4. | Cyprofuram + Tridemorph | 3 / 27 | 30 51 | +37 |
| 5. | Cyprofuram + Tridemorph | .6 / 24 | 30 46 | +32 |
| 6. | Cyprofuram + Tridemorph | 9 / 21 | 30 56 | +42 |
| 7. | Cyprofuram + Tridemorph | 12 / 18 | 30 52 | +38 |
| 8. | Cyprofuram + Tridemorph | 15 / 15 | 30 34 | +20 |
| 9. | Cyprofuram + Tridemorph | 18 / 12 | 30 36 | +22 |
| 10. | Cyprofuram + Tridemorph | 21 / 9 | 30 44 | +30 |
| 11. | Cyprofuram + | 24 | | |

-continued

| No. | Treatments Substances | Concentration mg/L | | Inhibition % | −MRV |
|---|---|---|---|---|---|
| | Tridemorph | 6 | } 30 | 29 | +15 |
| 12. | Cyprofuram + | 27 | } 30 | 20 | |
| | Tridemorph | 3 | | | |

LSD$_{5\%}$ = 5.9
MRV = Maximum response value according to the Horsfall's model for the demonstration of the synergistic interaction. The efficacy of combinations has been compared to that of the more potent combination partner.

EXAMPLE 18

Joint action of morpholine (tridemorph) and phenylamide (Ofurace) fungicides on the sporulation of *Plasmorpara halstedii* (Oomycetes, Peronosporales, Peronosporaceae).

*P. halstedii* is an obligate parasite of sunflower. It infects the host plant either through the soil (infection originated from oospores) or through the air (airborn infection originated from sporulating infected leaf areas), and introduced to new fields mainly with infected seeds (seed borne infection). Zoosporangia spread by wind can infect all parts of the plant, therefore the inhibition of sporulation is an important measure of the control of this pathogen.

All cultural techniques, treatments and the way of assessments were made as described in Example 4a.

The efficacy was expressed in the percent of inhibition.

| No | Treatment Substance | Concentration mg/L | | Inhibition % | −MRV |
|---|---|---|---|---|---|
| 1. | Tridemorph | 50 | | 0 | |
| 2. | Ofurace | 25 | | 21 | |
| 3. | Ofurace + | 6.25 | } 25 | 36 | +75 |
| | Tridemorph | 18.75 | | | |

LSD$_{5\%}$ = 5.9
MRV = Maximum response value according to the Horsfall's model for the demonstration of the synergistic interaction. The efficacy of combinations has been compared to that of the more potent combination partner.

EXAMPLE 19

Joint action of morpholine (tridemorph fungicide) and oxadixyl on the sporulation of *Plasmorpara halstedii* (Oomycetes, Peronosporales, Peronosporacease).

*P. halstedii* is an obligate parasite of sunflower. It infects the host plant either through the soil (infection originated from oospores) or through the air (airborn infection originated from sporulating infected leaf areas), and introduced to new fields mainly with infected seeds (seed borne infection). The zoosporangia spread by wind can infect all parts of the plant, therefore the inhibition of sporulation is an important measure of the control of this pathogen.

All cultural techniques, treatments and the way of assessments were made as described in Example 4a.

The efficacy was expressed in the percent of inhibition.

| No. | Treatments Substance | Concentration mg/L | | Inhibition % | −MRV |
|---|---|---|---|---|---|
| 1. | Tridemorph | 50 | | 0 | |
| 2. | Oxadixyl | 50 | | 18 | |
| 3. | Oxadixyl + | 10 | } 50 | 46 | +26 |
| | Tridemorph | 40 | | | |
| 4. | Oxadixyl + | 12.5 | } 50 | 50 | +36 |
| | Tridemorph | 37.5 | | | |
| 5. | Oxadixyl + | 25 | } 50 | 36 | +18 |
| | Tridemorph | 25 | | | |

LSD$_{5\%}$ = 5.9
MRV = Maximum response value according to the Horsfall's model for the demonstration of the synergistic interaction. The efficacy of combinations has been compared to that of the more potent combination partner.

EXAMPLE 20

Joint action of morpholine (tridemorph) and phenylamide (ofurace) fungicides on the vegetative growth of Phytophthora species (Oomycetes, Peronosporales, Pythiaceae).

*Phytophthora parasitica* f.sp. *nicotianae* var. *tomato* and *P. citricola* both are facultatively parasitic fungi able to infect their hosts either through the soil or through the air (airborn infection) causing root rot, leaf spots and fruit rot.

The inhibition of vegetative growth of both fungi was tested as described in Example 4b.

The efficacy was expressed in the percent of inhibition.

| | | | RESULTS | | | |
|---|---|---|---|---|---|---|
| | Treatment | Conc. | Inhibition of the growth of | | | |
| No | Substance | mg/L | P. citricola | −MRV | P. parasitica | −MRV |
| 1. | Tridemorph | 1 | 0 | | 3 | |
| 2. | Tridemorph | 5 | 14 | | 9 | |
| 3. | Tridemorph | 10 | 27 | | 14 | |
| 4. | Tridemorph | 50 | 75 | | 32 | |
| 5. | Tridemorph | 100 | 93 | | 40 | |
| 6. | Ofurace | 0.5 | 3 | | 25 | |
| 7. | Ofurace | 1 | 9 | | 40 | |
| 8. | Ofurace | 5 | 46 | | 76 | |
| 9. | Ofurace | 10 | 66 | | 87 | |
| 10. | Ofurace | 50 | 95 | | 98 | |
| 10. | Ofurace | 100 | 99 | | 100 | |
| 12. | O + T (1:4) | 0.5 | 10 | +7 | 52 | +27 |
| 13. | O + T (1:4) | 1 | 16 | +7 | 72 | +32 |
| 14. | O + T (1:4) | 5 | 62 | +20 | 98 | +23 |
| 15. | O + T (1:4) | 10 | 85 | +19 | 99 | +12 |

| | Treatment | Conc. | RESULTS Inhibition of the growth of | | | |
|---|---|---|---|---|---|---|
| No | Substance | mg/L | P. citricola | −MRV | P. parasitica | −MRV |
| 16. | O + T (1:4) | 50 | 99 | +4 | 100 | +2 |
| 17. | O + T (1:4) | 100 | 100 | +1 | 100 | — |

MRV = Maximum response value according to the Horsfall's model for demonstration of synergistic interaction. The efficacy of combinations has been compared to that of the more potent partner.
o = ofurace, T = tridemorph

CONCLUSION

Tridemorph and ofurace a synergistically interact in the inhibition of the vegetative growth of Phytophthoras.

EXAMPLE 21

The effect of oxadixyl, tridemorph and their combination on the late blight of tomato.

The four-leaf-stage tomato plants (*Lycopersicum esculentum* cv. Tamina) have been sprayed run off, and four hours later were infected with suspension of zoospores of *Phytophthora infestans* (Peronosporales). The plants next to infection were kept 24 hours in a moist chamber at 16°–18° C., then grown five days in greenhouse.

The degree of infection (DI %) was assessed on the basis of symptoms (Blighting or spotting on leaves). The efficacy of treatments was calculated using the following formula:

$$\text{Efficacy (\%)} = 100 - \frac{\text{DI on treated plants} \times 100}{\text{DI on untreated plants}}$$

| | Active agent, combination, resp. | RESULTS Concentration mg/L | DI % | Efficacy % | −MRV |
|---|---|---|---|---|---|
| 1. | Control | 0 | 88 ± 4 | | |
| 2. | Tridemorph | 5 | 86 ± 5 | 0 | |
| 3. | Oxadixyl | 5 | 59 ± 3 | 33 | |
| 4. | 2 + 3 (4:1) | 5 | 50 ± 2 | 43 | +10 |
| 5. | 2 + 3 (3:2) | 5 | 41 ± 3 | 55 | +22 |

EXAMPLE 22

Joint action of morpholine (tridemorph) and phenylamide fungicides on the vegetative growth of Phytophthora supp. (Oomycetes, Peronosporales, Pythiaceae).

*Phytophthora parasitica* f.sp. nicotinae var. tomato and *P. citricola* both are facultatively parasitic fungi able to infect their hosts either with mycelia or with asexual spores (soil born and airborn infections) causing serious loss of the yield before or after the harvesting.

The inhibition of vegetative growth of both fungi was tested as described in Example 4b. The $ED_{50}$ and $ED_{90}$ values were calculated by plotting efficacies on log/probit paper graphically. The degree of synergistic interaction was characterized by Comparative Toxicity Indices (CoTI) according to PEN (1952):

| | | RESULTS A Inhibition of the vegetative growth on | | | |
|---|---|---|---|---|---|
| | | P. citricola | | P. parasitica | |
| No | Substances | $ED_{50}$ | $ED_{90}$ mg/L | $ED_{50}$ | $ED_{90}$ mg/L |
| 1. | Tridemorph | 189.1 | 637.3 | 28.6 | 128.4 |
| 2. | Benalaxyl | 7.8 | 50.0 | 6.1 | 39.4 |
| 3. | Cyprofuram | 7.7 | 110.5 | 24.6 | 182.3 |
| 4. | Ofurace | 1.5 | 12.8 | 5.3 | 30.1 |
| 5. | Trid + Benal (4:1) | 1.2 | 6.8 | 1.7 | 7.8 |
| 5. | Trid + Cyprof (4:1) | 11.6 | 42.7 | 2.7 | 11.6 |
| 7. | Trid + Ofur (4:1) | 0.4 | 2.3 | 2.8 | 10.9 |

| | | B Comparative Toxicity Indices for | | | |
|---|---|---|---|---|---|
| | | P. citricola | | P. parasitica | |
| | | as compared on the basis of | | | |
| | Combinations | $ED_{50}$ | $ED_{90}$ | $ED_{50}$ | $ED_{90}$ |
| 1. | Tridemorph + Benalaxyl (4:1) | 5.46 | 5.62 | 1.93 | 2.26 |
| 2. | Tridemorph + Cyprofuram (4:1) | 0.58 | 1.52 | 2.62 | 2.34 |
| 3. | Tridemorph + Ofurace (4:1) | 3.46 | 5.07 | 1.06 | 1.42 |

EXAMPLE 23

The effect of chemicals on the elongation of sunflower hypocotyl following the treatment of germlings.

| | Chemical | Length of hypocotyl (cm) | |
|---|---|---|---|
| | | A[+] | B[++] |
| 1. | Control[+++] | 8.3 | 3.7 |
| 2. | Cyprofuram | 9.9 | 7.4 |
| 3. | LAB 149202F | 13.4 | 8.4 |
| 4. | Metalaxyl | 9.6 | 7.5 |
| 5. | Ofurace | 8.6 | 7.8 |
| 6. | RE 26745 | 11.6 | 6.7 |

[+] = Phenylamide applied along at 10 mg/L.
[++] = Penylamide and aldimorph in combination (10 + 40 mg/L)
[+++] = In the case of A no chemical was used, in the case of B 40 mg/L of aldimorph was only applied.
Note: All the procedure concerning chemical treatment and assessment were made as described in VIRANYI, F. and OROS, G.: Study of fungicidal effect in glasshouse against *Plasmopara halstedii* (Farlow) Berlese et de Toni. Növenyvedelem XXII, 1–10, (1986).
There was no correlation found between growth stimulation by phenylamides and their antagonistic effect on growth inhibition by aldimorph (r = 0.25).

What is claimed is:

1. A synergistic fungicidal composition which comprises:
 (A) N-cyclododecyl-2,6-dimethylmorpholine, or an agriculturally acceptable salt thereof, and
 (B) 2-chloro-N-(2,6-dimethylphenyl)-N-(tetrahydro-2-oxo-3-furanyl)-acetamide, wherein the weight ratio of the Compound (A) to the Compound (B) is 4:1 to 1:1.

2. A synergistic fungicidal composition which comprises:

(A) N-tridecyl-2,6-dimethylmorpholine, or an agriculturally acceptable salt thereof, and (B) 2-chloro-N-(2,6-dimethylphenyl)-N-(tetrahydro-2-oxo-3-furanyl)-acetamide, wherein the weight ratio of the Compound (A) to the Compound (B) is 5:1 to 1:1.

3. The synergistic fungicidal composition defined in claim 2 wherein the weight ratio of the Compound (A) and the Compound (B) is 5:1 to 3:1.

4. The synergistic fungicidal composition defined in claim 2 wherein the weight ratio of the Compound (A) and the Compound (B) is 4:1 to 3:1.

5. A method of protecting a cultivated plant from a fungal infection which comprises the step of applying to said plant, a synergistically, fungicidally effective amount of the synergistic fungicidal composition defined in claim 1.

6. A method of protecting a cultivated plant from a fungal infection which comprises the step of applying to said plant, a synergistically, fungicidally effective amount of the synergistic fungicidal composition defined in claim 2.

* * * * *